(12) United States Patent
Rijcken et al.

(10) Patent No.: US 10,034,835 B2
(45) Date of Patent: *Jul. 31, 2018

(54) CROSSLINKED VACCINATION COMPOSITION

(71) Applicant: CRISTAL DELIVERY B.V., Maastricht (NL)

(72) Inventors: Cristianne Johanna Ferdinand Rijcken, Maastricht (NL); Josephus Johannes Maria Holthuis, Maastricht (NL)

(73) Assignee: CRISTAL DELIVERY B.V., Maastricht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/364,087

(22) Filed: Nov. 29, 2016

(65) Prior Publication Data

US 2017/0079918 A1    Mar. 23, 2017

Related U.S. Application Data

(63) Continuation of application No. 14/775,642, filed as application No. PCT/NL2014/050139 on Mar. 10, 2014, now Pat. No. 9,539,212.

(30) Foreign Application Priority Data

Mar. 11, 2013  (NL) .................................. 2010427

(51) Int. Cl.
    *A61K 9/16*    (2006.01)
    *A61K 47/48*   (2006.01)
    (Continued)

(52) U.S. Cl.
    CPC ............ *A61K 9/1635* (2013.01); *A61K 9/107* (2013.01); *A61K 9/1682* (2013.01);
    (Continued)

(58) Field of Classification Search
    CPC .... A61K 9/1694; A61K 38/04; A61K 39/385; A61K 47/4833
    See application file for complete search history.

(56) References Cited

U.S. PATENT DOCUMENTS 7,425,581 B2    9/2008  Hennink et al.

FOREIGN PATENT DOCUMENTS

| EP | 1776400 | 4/2007 |
|----|---------|--------|
| WO | WO-2010/033022 | 3/2010 |
| WO | WO-2014/142653 | 9/2014 |

OTHER PUBLICATIONS

Bontha et al., "Polymer micelles with cross-linked ionic cores for delivery of anticancer drugs," J Control Release (2006) 114(2):163-174.

(Continued)

*Primary Examiner* — Carlos A Azpuru
(74) *Attorney, Agent, or Firm* — Morrison & Foerster LLP (57) ABSTRACT

The present invention is directed to vaccination composition comprising a particle comprising a polymer matrix incorporating an adjuvant and/or an antigen, to method of making them and use. Particularly, the present invention results in adjuvants and/or antigens, covalently entrapped in or coupled to polymer carriers or polymeric devices, such as micelles, nanoparticles, microspheres and other types of polymer devices for controlled release; the adjuvant and/or antigen are covalently bonded in or to the polymer carriers or polymeric devices.

19 Claims, 2 Drawing Sheets

(51) Int. Cl.

| | | |
|---|---|---|
| A61K 39/385 | (2006.01) | |
| A61K 38/04 | (2006.01) | |
| A61K 39/00 | (2006.01) | |
| A61K 9/107 | (2006.01) | |

(52) U.S. Cl.
CPC ............ *A61K 9/1694* (2013.01); *A61K 38/04* (2013.01); *A61K 39/0013* (2013.01); *A61K 39/385* (2013.01); *A61K 47/488* (2013.01); *A61K 47/4833* (2013.01); *A61K 47/48176* (2013.01); *A61K 2039/6093* (2013.01); *A61K 2039/627* (2013.01)

(56) References Cited

OTHER PUBLICATIONS

Censi et al., "In-situ forming hydrogels by simultaneous thermal gelling and Michael addition reaction between methacrylate bearing thermosensitive triblock copolymers and thiolated hyaluronan," J Control Release (2010) 148(1):e28-29.

Censi et al., "Photopolymerized thermosensitive hydrogels for tailorable diffusion-controlled protein delivery," J Control Release (2009) 140(3):230-236.

Crielaard et al., "Glucocorticoid-loaded core-cross-linked polymeric micelles with tailorable release kinetics for targeted therapy of rheumatoid arthritis," Angew Chem Int Ed Engl (2012) 51(29):7254-7258.

Foged et al., "License to kill: Formulation requirements for optimal priming of CD8(+) CTL responses with particulate vaccine delivery systems," Eur J Pharm Sci (2012) 45(4):482-491.

Hao et al., "Peptide crosslinked micelles: a new strategy for the design and synthesis of peptide vaccines," Int J Nanomedicine (2006) 1:97-103.

Hirosue et al., "Antigen delivery to dendritic cells by poly(propylene sulfide) nanoparticles with disulfide conjugated peptides: Cross-presentation and T cell activation," Vaccine (2010) 28(50):7897-7906.

Hu et al., "Core crosslinking of biodegradable block copolymer micelles based on poly(ester carbonate)," Macromol Biosci (2009) 9(5):456-463.

Kim et al., "Core-stabilized Polymeric Micelle as Potential Drug Carrier: Increased Solubilization of Taxol," Polym Adv Technol (1999) 10:647-754.

Kim et al., "Polymer micelles with cross-linked polyanion core for delivery of a cationic drug doxorubicin," J Control Release (2009) 138(3):197-204.

Kunda et al., "Nanocarriers targeting dendritic cells for pulmonary vaccine delivery," Pharm Res (2013) 30(2):325-341.

Lee et al., "Amphiphilic poly(D,L-lactic acid)/poly(ethylene glycol)/poly(D,L-lactic acid) nanogels for controlled release of hydrophobic drugs," Macromol Biosci (2006) 6(10):846-854.

Lee et al., "Charge-conversional polyionic complex micelles-efficient nanocarriers for protein delivery into cytoplasm," Angew Chem Int Ed Engl (2009) 48(29):5309-5312.

Mansuroglu et al., "Characterization of water-soluble conjugates of polyacrylic acid and antigenic peptide of FMDV by size exclusion chromatography with quadruple detection," Materials Science and Engineering (2012) 112-118.

Mohanan et al., "Administration routes affect the quality of immune responses: A cross-sectional evaluation of particulate antigen-delivery systems," J Control Release (2010) 147(3):342-349.

Miyata et al., "Freeze-dried formulations for in vivo gene delivery of PEGylated polyplex micelles with disulfide crosslinked cores to the liver," J Control Release (2005) 109(1-3):15-23.

Nishiyama et al., "Novel cisplatin-incorporated polymeric micelles can eradicate solid tumors in mice," Cancer Res (2003) 63(24):8977-8983.

Rydell et al., "Oral vaccination against diphtheria using polyacryl starch microparticles as adjuvant," Vaccine (2004) 22(9-10)1265-1274.

CROSSLINKED VACCINATION COMPOSITION

CROSS-REFERENCE TO RELATED APPLICATION

This application is a continuation of U.S. Ser. No. 14/775,642 (now allowed) having an international filing date of 10 Mar. 2014, which is the national phase of PCT application PCT/NL2014/050139 having an international filing date of 10 Mar. 2014, which claims benefit of Dutch patent application No. 2010427 filed 11 Mar. 2013. The contents of the above patent applications are incorporated by reference herein in their entirety.

FIELD OF THE INVENTION

The present invention relates to vaccination composition comprising a particle for controlled release of antigens and/or adjuvants.

BACKGROUND

Vaccination is a powerful method against diseases. According to the World Health Organization (WHO), around 2.5 million children's lives are saved each year due to the availability of vaccines against a variety of antigens. Vaccines are not only used in a preventive manner but also therapeutically as well e.g. in oncology or in Alzheimer's disease. The immune system works by first capturing antigens, subsequently amplifying a complex network of specialized cells that are adept at clearing pathogens, and ultimately creating an immunological memory of that agent in the event of future exposure. Antigen presenting cells, (APCs), such as B cells, macrophages and dendritic cells (DCs), take up antigens and process these and present fragments of these antigens on the surface through MHC class I and II pathways for recognition by the T-cell receptors present on the T-cells. DCs are unique in their ability to activate naive T cells. Dendritic Cells (DC) play therefore a central role in the vaccination process. This process of antigen presentation typically takes place in the regional lymph node after chemokine dependent migration of the antigen loaded DC. Also, antigen presenting cells (APCs) perceive danger signals from cells and offer co-stimulatory signals through co-stimulatory molecules present on their surface for recognition by receptors on recirculating T-cells to initiate an immune response in the lymph node. Upon encountering the danger signals, immature DCs change to a mature stage where they present the antigen on their surface. This step is usually concurrent with the migration of DCs from peripheral tissue to the lymph node for T-cell activation. It is believed that soon after antigen presentation, the DCs undergo apoptosis in the lymph nodes.

In addition, to antigens, vaccine composition often comprise adjuvants. Adjuvants are agents that enhance or boost the immune response of a recipient to a administered antigen. For instance, subunit vaccines, require the addition of adjuvants for a proper immune response.

Nanoparticles and microparticles have been used in vaccine compositions. Biodegradable nanoparticles comprising of poly (D,L-lactic-co-glycolic-acid) (PLGA) have been used to encapsulate antigens or adjuvants. Also polystyrene beads with ovalbumin (OVA) have been tested.

It was disclosed that Micelles (Peptide Cross-linked micelles-PCMs) PCMs that are composed of block copolymers and encapsulate immuno stimulatory DNA in the core and bind peptide antigens through disulphide linkages. In the presence of a high concentration of glutathione they deliver antigenic peptides and immuno stimulatory DNA to APCs (Hao et al, Int J Nanomedicine. 2006; 1:97-103, Hirosue et al, Vaccine 28 (2010) 7897-7906). However, disulphide bridges do not allow for controlled release.

However, the use of nanoparticles in vaccination still has several bottlenecks. It is e.g. required that sufficient antigens should be presented to dendritic cells (DC) in a way that leads to a sufficient immune activation. Thereby preferably avoiding tolerance or auto immunity. Often, several vaccinations are needed to require long immunisation.

Furthermore, for each purpose, the vaccine composition needs optimisation. It requires, the appropriate selection of immunisation methods and/or adjuvants. It depends very much on the type of use, preventive, or therapeutic. Moreover, one tries to avoid unwanted side effects such as autoimmune disease, and tolerance.

It is also seen that the majority of nanoparticles are taken up by macrophages upon administration while the target is preferably DCs. Another disadvantage of the current nano- and microparticle is that they comprise physically encapsulated antigen and/or adjuvant, i.e. the antigen and/or adjuvant is not covalently entrapped by the nano- or microparticle. This means that there is no or minimal control over the release profile while this is crucial for best immune system presentation/activation. It is often seen that there is a burst release of the antigen and/or adjuvant when the particles are administered because of the inherent biological instability of the nano- or microparticles of the prior art. The release of the antigen and/or adjuvant takes place at the site of administration instead of the site/cells where it is most useful to present the adjuvant and antigen. Furthermore, the nanoparticles in the prior art themselves are all physical assemblies, meaning the forces holding the particle together are physical forces and not covalent linked, and thus often these particle are unstable. In addition, antigens and/or adjuvants are mostly physically adsorbed to the nanoparticle surface, which is much less stable than covalent bonding and does not allow for a controlled release or to a much lower extent. Moreover, although the nanoparticles themselves are described as single molecular entities, the structural integrity of these nanoparticles is largely unknown, because of the method of production and the physical assembly and encapsulation. Often, these nanoparticles to a large extent disrupt after administration to the animals. The instability of the nanoparticle, may result in that not all antigen is associated with the carrier. For example, it was shown that 25% of the OVA was not associated with the liposomes. Trimethylchitosan (TMC) nanoparticles and showed a burst release of approx. 20% OVA within the first day, followed by no further detectable release of OVA over three weeks. Similarly, PLGA microspheres produced an immediate OVA burst release, which amounted to 32% and 10% of the total dose for the microspheres loaded with OVA alone or with both OVA and CpG, respectively. No further protein release was detectable during the subsequent three weeks. (Mohanan et al, J. Control Rel (2010) vol 147:3; 342-349).

Another disadvantage is that the production of the nanoparticle may affect the antigen structure, e.g. see the advantages and disadvantages of nanoparticle preparation methods (Kunda et al, Pharm Res (2013) 30:325-341).

It appears that the uptake of nanoparticle in target cells is largely size and composition dependent, thus requiring full control of the size and composition. For many nanoparticles, and methods of production in the prior art however it is not possible to control the size and/or composition. Indeed, most of the particles of the prior art show a large distribution in size, thereby rendering a vaccine composition based on the particles heterogeneous, or requiring further purification. Furthermore for vaccination purposes there has to be a tight control over the encapsulation of antigen and/or adjuvant, and/or attachment of the targeting agent to ensure batch to batch reproducibility. Most of the nanoparticles in the prior art do not enable such a tight control, and are therefore not suitable for vaccination purposes and to generate a robust therapeutic response.

Often, for the nanoparticles of the prior art, the immune response is not long enough, e.g. because of the burst release, and thus additional boosting schedules are required for sufficient immune response.

WO2010/138193 is directed to compositions of synthetic nanocarriers that may target sites of action in cells, such as antigen presenting cells and comprise immunomodulatory agents that dissociate from the synthetic nanocarriers in a pH sensitive manner. The synthetic nanocarriers of WO2010/138193 are preferentially taken up by APCs. Upon being taken up by the APC, the synthetic nanocarriers are presumed to be endocytosed into an endosomal/lysosomal compartment where the pH becomes more acidic, as opposed to the neutral pH outside the cells. Under these conditions, the immunomodulatory agent exhibits a pH sensitive dissociation from the synthetic nanocarrier and is released from the synthetic nanocarrier. The immunomodulatory agent is then free to interact with receptors associated with the endosome/lysosome and stimulate a desired immune response. However WO2010/138193 does not discloses cross-linking of the polymers when the immunomodulatory agent is present. There is no disclosure of a system wherein the immunomodulatory agent is covalently entrapped into the nanoparticle. In WO2010/138193 particles are made by first conjugating the immunomodulatory agent to the polymer and then make nanoparticles of the immunomodulatory agent-polymer complex. The system of WO2010/138193 thus requires different routes for conjugation for each different immunomodulatory agent.

US2009/011993 is directed to particles that deliver active agents such as vaccines, immune modulatory agents and/or drugs that target antigen presenting cells. US2009/011993 discloses a new type of hydrophobic polymers comprising ketal groups in the polymer backbone wherein the ketal groups are arranged in a way such that both oxygen atoms are located in the polymer backbone. US2009/011993 discloses the use of an external crosslinking agent to cross-link the polymers to the immune modulatory agents, and does not disclose a crosslinking step of the polymers in the presence of immune modulatory agents.

Unfortunately there seems to be no universal formulation that can be universally be applied to various (subunit) vaccines. For most systems of the prior art, the particles and conjugation needs an optimisation for each different immunomodulatory agent. This requires extensive research for each new particle with a another immunomodulatory agent, and creates differences between the different immunomodulatory agents. The optimum formulation preferably depends on the type of response required for protective immunity and the intended route of administration. Various formulation aspects, such as particles size, choice of adjuvant, and co-localization of antigen and adjuvant, are preferably adjusted based on the selected administration route. The nanoparticles described in the prior art may be suitable for one particular antigen and/or adjuvant and for one particular route of administration, but are often unsuitable for another antigen/adjuvant and/or other route of administration. Thus for different vaccination routes, each time a different nanoparticle has to be developed.

WO 2010/033022 and WO2013/002636 disclose a controlled release system comprising drugs such as dexamethasone and paclitaxel, however they do not disclose that antigens and/or adjuvants may be entrapped in the polymeric matrix particles.

WO2012/039602 discloses biodegradable linker molecules that may be used in a covalent polymer matrix particle such as disclosed in WO 2010/033022 and WO2013/002636. WO2012/039602 does not disclose antigens or adjuvants in such a system.

It is therefore an object of the present invention to provide a vaccination composition. It is furthermore an object of the present invention to provide a vaccination composition that is easily adjustable for different administration routes. In addition, the vaccination composition preferably provides a system with covalent bonding of an antigen and/or adjuvant thereby ensuring full control over the local and time-spatial exposure to adjuvant or antigen. Another object of the invention is to provide a vaccination composition comprising nano- and/or microparticles. Furthermore, another object of the present invention is to provide a vaccine composition wherein the controlled release particles have a narrow size distribution. Yet another object of the invention is to provide a vaccination composition that may accommodate different antigens and/or adjuvants, e.g. both hydrophilic and hydrophobic compounds and over a large size range. Moreover, another object of the invention is to provide a vaccination composition wherein the release of the adjuvant and/or antigen can be controlled. Another object of the invention is to provide a vaccination composition wherein each entrapped adjuvant and/or antigen has its own unique release profile. Even another object of the present invention is to provide a vaccination composition that comprises targeting agents covalently attached to the particle, e.g. to its surface. The targeting agent may direct the particle of the present invention to the cells or site of interest, such as APCs. Moreover, another object of the invention is to provide a vaccination system wherein the antigen and/or adjuvant may be encapsulated but may also be present on the surface of a particle or both. Yet another object of the invention is to provide method for producing the vaccination composition that is safe and/or non-destructive for the antigen and/or adjuvant.

The present invention provides a vaccination composition that meets one or more of the above mentioned objects.

SUMMARY OF THE INVENTION

In a first aspect, the present invention provides a vaccination composition comprising a particle comprising an antigen and/or a adjuvant wherein the particle is obtainable by a method comprising the steps of:
(i) mixing an antigen and/or adjuvant comprising a reactive moiety with an aqueous solution or dispersion comprising polymer chains comprising at least one reactive moiety, capable of reacting with the reactive moiety of the adjuvant and/or antigen, the polymer chains further being capable of cross-linking intra- or intermolecularly; and
(ii) subjecting this mixture to conditions wherein the polymers self-assemble into particles, with the antigen and/or adjuvant encapsulated in the core of the micelles
(iii) subjecting the particle mixture to cross-linking forming a polymer matrix under such conditions that simultaneous with the formation of the polymer matrix the adjuvant and/or antigen is entrapped in this polymer matrix, that is in the polymeric network formed.

The polymer matrix is the polymeric network formed. The antigen and/or adjuvant are thus entrapped in the polymer matrix, in the polymer network formed by the crosslinking. The antigen and/or adjuvant cross-link to the polymer chains and thus form also part of the polymer network and the polymer matrix.

In a second aspect, the present invention provides a method to produce a vaccination composition comprising a particle comprising an antigen and/or a adjuvant, said method comprising the steps of:

i) mixing an antigen and/or adjuvant comprising a reactive moiety with an aqueous solution or dispersion comprising polymer chains comprising at least one reactive moiety capable of reacting with the reactive moiety of the adjuvant and/or antigen, the polymer chains further being capable of cross-linking intra- or intermolecularly; and (ii) subjecting this mixture to conditions wherein the polymers self-assemble into particles, with the antigen and/or adjuvant encapsulated in the core of the micelles (iii) subjecting the particle mixture from step (ii) to cross-linking forming a polymer matrix under such conditions that simultaneous with the formation of the polymer matrix the adjuvant and/or antigen is entrapped in this polymer matrix, that is in the polymeric network formed.

In a further aspect of the invention, the present invention provides a method to produce a vaccination composition comprising a particle comprising an antigen and/or a adjuvant, said method comprising the steps of:

(i) providing an aqueous solution or dispersion comprising polymer chains comprising at least one reactive moiety, capable of reacting with the reactive moiety of the adjuvant and/or antigen, the polymer chains further being capable of cross-linking intra- or intermolecularly; and (ii) subjecting this mixture to conditions whereby the polymers self-assemble into particles, and, (iii) mixing the particle from step (ii) with a solution comprising an adjuvant and/or antigen such that the antigen and/or adjuvant is encapsulated in the particle, and;

(iv) subjecting the particle mixture from step (iii) to cross-linking forming a polymer matrix under such conditions that simultaneous with the formation of the polymer matrix the adjuvant and/or antigen is entrapped in this polymer matrix, that is in the polymeric network formed.

Suitably, in all aspects and/or embodiments of the invention, after crosslinking, a targeting agent and/or an antigen and/or an adjuvant is conjugated to the surface of the generated particles. Preferably the conjugation is covalent. Suitably the polymer chains comprise reactive moieties that do not react in the cross-linking step and may be used to link a targeting agent and/or an antigen and/or an adjuvant to the surface of the formed and cross-linked particle. Alternatively, after the crosslinking, additional linking groups are attached to the surface of the generated cross-linked particles that may further react to conjugate a targeting agent and/or an antigen and/or an adjuvant to the surface of the cross-linked particle. Also reactive moieties on the polymer chains may be blocked during the cross-linking step and deblocked when the polymer network has formed. These deblocked reactive moieties may then be reacted with a targeting agent and/or an antigen and/or an adjuvant such that these will be attached to the surface of the cross-linked particle. In addition, the targeting agent and/or antigen and/or adjuvant may comprise a reactive moiety that is able to conjugate to the polymer chains of the cross-linked particles.

In another aspect, the invention is related to the use of a vaccine composition in a prophylactic manner.

In another aspect, the invention is related to a vaccine composition for use as a medicine Yet another aspect of the invention is related to a method of treatment using the vaccine composition of the invention.

In all aspects and/or embodiments of the invention, the polymer comprises at least one reactive moiety per polymer chain. Also in all aspects and/or embodiments of the invention the adjuvant and/or antigen comprise at least one reactive moiety. Advantageously the adjuvant and/or antigen are covalently entrapped in the polymer matrix during the cross-linking step. During the cross-linking step, the polymers form a network together with the adjuvant and/or antigen, which form the polymer matrix which entrap the antigen and/or adjuvant. The antigen and/or adjuvant are thus also cross-linked to the polymers during the cross-linking step, such that the antigen and/or adjuvant are covalently linked to the polymer chains, and form part of the network formed. Simultaneously the polymer chains are cross-linked to each other to form a polymer network, the polymer and entrapped adjuvant and/or antigen form the polymer matrix.

DETAILED DESCRIPTION

The present invention provides for a vaccination composition comprising a particle comprising an antigen and/or a adjuvant. The particle may covalently entrap an antigen and/or an adjuvant on the inside of the particle. In addition, it may also provide for an antigen and/or adjuvant on the outer surface of the particle. The controlled release particle of the present invention may simultaneously carry several different antigens and/or adjuvants in one particle, thereby ensuring that the different antigen and/or adjuvant are released at the same site. It may also be possible to target the controlled release particle to a specific target site, for example by conjugation of a specific targeting agent to the outer surface of the cross-linked particle. In addition, the release profile of the adjuvant and/or antigen may be tuned as desired. The particle of the present invention may use different linkers for different molecules, thereby providing the desired release for each adjuvant and/or antigen. One system may be produced with different molecules, each having its own release profile. The system of the present invention provides a true tunable system for optimisation of the (therapeutic) effect.

The vaccination composition of the present invention is unique as it comprises the essential required elements for tailor-made optimised vaccination products. The vaccination composition of the present invention allows for stimulation of the dendritic cells in an optimal manner by full control over:

Range of different linkers, allowing for custom-made release of each individual core entrapped/surface conjugated compound, either continuous or via a pulsatile manner. Burst release may be prevented, as well as release at unwanted sites of the body. This may reduce unwanted side effects, such tolerance, and/or over reaction to the antigen and/or adjuvant.

Possibility of a range of reactive moieties at the outer surface of the particles that allow for the covalent conjugation of one or more specific molecule(s), either being an antigen, adjuvant or a cellular targeting agent or any combination thereof.

The method of making the particle provides particles with a specific size with a very small particle size distribution, which allows for clear evaluation of specific effects of the vaccination composition and prevents unwanted disturbance side effects by a small percentage of very large or very small particles as present in more heterogeneous nanoparticle dispersion such as disclosed in the prior art. From the prior art is appears that for each purpose the vaccination composition needs optimisation. The present system, due to its homogeneity, stability, and purity, offers the advantage that one can truly optimise the vaccination composition. Vaccine compositions may be made with no impurities such as much larger or smaller particle, or free antigen and/or adjuvant. As the antigen or adjuvant is covalently entrapped the particles may be easily purified from free antigen and/or adjuvant. The particles are also stable over time during storage as the adjuvant and/or antigen are covalently linked to the polymer matrix. In this way one is sure that the observed effect is from the particle intended and not from an impurity.

Co-delivery of antigen(s) and adjuvant(s) to evoke the best effective immune response. The present particles may comprise both antigens and adjuvants. Both the antigen and adjuvant may entrapped in the polymer matrix but also either the antigen or the adjuvant or both may be linked to the surface of the polymer particles. In addition, more than one adjuvant and/or antigen may be entrapped or bound to the surface of the polymer particle. The present method to produce the particles provides the flexibility to produce particles with several different combination of antigens and adjuvants being present inside the polymer matrix as well as on the surface of the particles formed. It has become clear that most efficient adjuvants are obtained by combining delivery systems and immunopotentiators and thereby exploiting their synergistic actions. Certain types of combination adjuvants consisting of particulate antigen delivery systems and immunopotentiating compounds have demonstrated the potential to generate strong CD8+ T-cell responses in both animal studies as well as in human clinical trials. (Foged et al, EJPS, 2012)

In addition to stimulating potent CD8+ T-cell responses, co-administration of immunopotentiator and delivery system can also in certain cases be beneficial from a safety point of view. In animal models, adjuvants based on soluble TLR ligands have been associated with induction of systemic effects e.g. secretion of toxic amounts of tumour necrosis factor α. This strong pro-inflammatory response seen upon injection of soluble TLR agonists occurs presumably due to the activation of the entire APC population, whereas a delivery system can focus the immunopotentiating effect to a minor proportion of the entire APC population and thereby prevent systemic adverse effects. So, the particles of the present invention provide a method for focusing the activity of immunopotentiators thereby rendering these potent substances innocuous. (Foged et al, EJPS, 2012)

The vaccine composition of the present invention may promote the induction of long-lived CD8+ memory T cells (Foged et al, EJPS, 2012).

The vaccine composition of the present invention may induce cross penetration phenomenon. The particles of the present invention may not only stimulate humoral immune response but also a cellular response.

After crosslinking and/or surface modification, the particle with antigen and/or adjuvant is truly one single macromolecule that allows for ease of purification. This high purity is not only essential to evaluate the underlying mechanism of action with regard to immunogenic activation in detail, but also represents a major advancement in terms of vaccine safety and pharmaceutical characterisation.

The present invention allows for a range of different crosslinking strategies, and that also allows for the entrapment of fragile molecules, such as peptides and proteins and other sensitive molecules.

The present invention allows for entrapment of a range of compounds, either hydrophilic as well as hydrophobic, and over a large size range. The present inventive particles are not restricted to hydrophilic or hydrophobic active agents. The cross-linking of the adjuvant and/or antigen to the polymer matrix allows both hydrophobic and hydrophilic adjuvants and antigens to be entrapped into the polymer matrix.

The synthesis procedure of the current controlled release particle may be very mild thereby assuring that the antigen(s) and/or adjuvants are fully preserved. Non-radical crosslinking may be employed thereby saving sensitive adjuvants and/or antigens.

The antigen is often a protein or peptide and may be susceptible to chemical and enzymatic degradation as well as physical alteration like aggregation or precipitation. The vaccination composition of the present invention may provide entrapment of antigen(s) thereby protecting them against (enzymatic) degradation after introduction to the body. The particles may be very dense, thereby inhibiting penetration of enzymes to the core of the particle, and thus effectively protecting the proteinaceous antigens.

The vaccine composition of the invention may be compact and intact, thus limiting macrophage uptake, so more DC targeting is possible. The particles of the invention have shown a long blood residence as well as high accumulation in tumour and in inflamed tissue.

The particles of the invention are initially stable due to the crosslinking, but are also in time biodegradable. The stability prevents a burst release, and keeps the antigen and/or adjuvant longer in the circulation, thereby increasing the possibility to activate the right target cells over a longer term period. In time, the entrapped compounds, such as antigen and/or adjuvant, are being released. In addition, the particles of the present invention disintegrate into small fragments.

In the vaccine composition of the invention it is possible to tune the linker type and thus particle with long(er) lasting antigen and/or adjuvant exposure may be made.

Due to the entrapment or conjugation to the surface the vaccine composition of the invention may require less antigen material for an immune response than vaccines with soluble antigen(s). In addition, targeting agents may be linked to the surface ensuring that the vaccine particles reach the target of interest.

The particles of the present invention are easily up scalable by a GMP-compatible 3-step approach to generate a whole plethora of particles:

It is possible to conjugate the antigen and adjuvant with different linkers. Different release profiles for the adjuvants and/or antigens are then possible. Using different linkers for different adjuvants and/or antigens also allow different reactive moieties on the antigen and/or adjuvant. This provides more control and linker specificity for derivative formation and/or purification and allows greater flexibility.

The method of the present invention is very flexible. It provides the synthesis of particles, having covalent conjugation antigens and/or adjuvants and additionally covalent conjugation of additional antigen, adjuvant and/or targeting agents to the surface.

The method of the present invention allows easy purification to remove any non-covalently entrapped antigen, adjuvant and/or ligands as the antigen of interest is covalently entrapped and thus stabile in the particles of the invention. The vaccine composition of the invention is very controllable and also broadly applicable, with high batch to batch reproducibility that allow for clear evaluation of 1 parameter at a time. This will ease the optimisation of the production as well as the optimisation of the therapeutic use.

In accordance with the present invention, the vaccination composition comprises a particle. Particularly, the present invention results in antigens and/or adjuvants, entrapped, preferably covalently, in or otherwise incorporated in or coupled to polymer carriers or polymeric devices, such as micelles, nanoparticles, microspheres, hydrogels and other types of polymer carriers or devices for vaccination; the antigens and/or adjuvants are covalently entrapped within the particle and/or bonded to the polymeric devices or carriers.

In a preferred embodiment, the particle is a controlled release system, and may encompass all kinds of controlled release, including slow release, sustained, pulsatile and delayed release.

For the present invention it should be understood that the particle may a nanoparticle and/or a microparticle.

In general, particles are classified according to diameter. Coarse particles cover a range between 10,000 and 2,500 nanometers. Fine particles, such as microparticles are sized between 2,500 and 100 nanometers. Ultrafine particles, such as nanoparticles are sized between 1 and 100 nanometers. For the present invention, microparticle range in size of between 100 and 0.5 micrometer, preferably between 50 and 1 micrometer, more preferably between 25 and 0.5 micrometer, and more preferably between 10 and 0.1 micrometer. Nanoparticles may range in size between 0.1 and 1000 nanometer, preferably between 1 and 500 nanometer, more preferably between 5 and 250 nanometer, more preferably between 10 and 200 nanometer, and more preferably between 30 and 150 nanometer. The size may influence the ability to be taken up by target cells. Generally virus-sized particles in the size range of 20 to 200 nm are usually taken up by endocytosis, resulting in a cellular-based immune response, whereas particles with sizes between 500 nm and 5 micron are mainly taken up by phagocytosis and/or macro-pinocytosis and are more likely to promote a humoral immune response. Specific cells usually have a upper and lower limit size for particles that may be taken up. A skilled person knows how to tune this. Alternatively, if one wishes that certain cells do not take up the particles of the invention, a skilled person may choose for a size that is outside the range for these cells. The particles of the present invention may be tuned to a desired size, enabling to target specific cells. In addition, the particles made by the methods of the invention have a narrow distribution so that a large part of the particles have the desired particle size and thus can target the desired cells.

In a preferred embodiment, the particles of the present invention have a very narrow size distribution, meaning that the larger part of the particles have a the same size. Preferably the particles have polydispersity index (DPI) of less than 0.5, more preferably less than 0.4, even more preferably less than 0.3, more preferably less than 0.2 and most preferably less than 0.1, or even less than 0.05.

Nanoparticulate vaccine compositions such as micelles, are considered to be promising candidates for immunization against diseases. The particle of the present invention may contain a broad variety of antigens and/or adjuvants including both hydrophobic and hydrophilic compounds. A suitable particle is described in WO 2010/033022. In the particle of the present invention and/or embodiment thereof antigens and/or adjuvants are first non-covalently entrapped in polymer phases, and especially in polymer-rich phases, in an aqueous environment, and subsequently are covalently conjugated to a 3D-polymer network.

In step (ii), formation of the particles, the antigen and/or antigen are physically, or non-covalently entrapped. Or in the alternative method, in step (iii) wherein the adjuvant and/or antigen are mixed with the formed particle, the antigen and/or adjuvant are physically, or non-covalently entrapped. In the crosslinking step, the antigen and/or adjuvant are covalently entrapped, rendering a particle wherein the antigen and/or adjuvant is covalently entrapped in the inside of the particle. It should be noted that the prior art discloses systems wherein first a cross-linking step is performed without the present of the antigen and/or adjuvant. In the invention of the application, the adjuvant and/or antigen are present during the cross-linking step thereby covalently linking the adjuvant and/or antigen to the polymer matrix. Also when linking the adjuvant and/or antigen to the surface of the particle, the adjuvant and/or antigen is covalently linked to the polymer matrix of the particle.

Advantages of the covalent entrapment of antigens and adjuvants in a polymeric network include no burst release, but displays a sustained exposure, thus decreasing the frequency of administration, releases of the antigen and/or adjuvant in time with fully tunable kinetics, allows entrapment of diverse antigens and/or diverse adjuvants;

including more than 1 type of antigen and/or adjuvant, potentially with different release rates, tunable properties, the particles may be surface modified by conjugation of targeting agent, such as ligands, e.g. for actively targeting to specific cells, homogenous and controllable sized particles with low polydispersity index, biocompatible and degrades into non-toxic fragments that are cleared from the body without adverse effects, easily sterilised by filtration through 0.22 μm and easy storage as frozen of lyophilised formulation.

Peptides as well as other larger and/or fragile molecules are mentioned as possible antigens and/or adjuvants.

The particle of the present invention and/or embodiments thereof are prepared by first mixing an antigen and/or adjuvant with a polymer and then subsequently cross-linking the polymer to form a polymer matrix. The crosslinking may be done with polymer and adjuvant and/or antigen each derivatised with polymerisable moieties and in the presence of free-radical initiators, but also other types of covalent conjugation linker are possible.

Particles with covalently entrapped and/or conjugated antigens and/or adjuvants may have several advantages as explained above. The resulting vaccine compositions may have therapeutic, curative or prophylactic properties. The particle of the present invention and/or embodiments thereof may provide a tunable system for providing the adjuvant and/or antigen to the location where it is needed. In addition, the particle may be decorated with antigens and/or other agents such as ligands, to target to a desired location and/or particular cell type. Entrapment of antigens and/or adjuvants in a particle may make these compounds suitable for vaccination, e.g. by oral or subcutaneous administration.

Antigens are often proteinaceous and thus vulnerable. Crosslinking of polymers may be carried out by free radical cross-linking. Free radical cross-linking may potentially harm the antigen, and may thus not be preferred.

Most non-free radical cross-liking is not propagating, forming only 1 to 1 reactions.

In step (i) the polymer chains preferably interact with each other (see herein-below) forming polymer sub phases in an aqueous phase. That is, relatively, polymer chain-rich and relatively polymer chain-poor phases are created. In a preferred embodiment, the antigen and/or adjuvant is present in the polymer chain rich phases. A sub-location of antigen and/or adjuvant in polymer chain rich sub-phases occurs based on physical interactions between the antigen and/or adjuvant and the polymer chains.

In step (i), the antigen and/or adjuvant do not form covalent conjugates with the polymer chains. Only in the cross-linking step (ii) or (iii) the antigen and/or adjuvant and the polymer chains together form a 3D-network.

The antigen and/or adjuvant are covalently bonded to the polymer carrier, preferably via a linker molecule, simultaneously with the cross-linking of the polymers forming the polymeric carrier or device. The cross-linked antigen and/or adjuvant-polymer conjugates which are formed in step (ii) or (iii) exhibit a higher thermodynamic stability than the non-cross-linked polymer particles. In addition, the entrapped antigen and/or adjuvant molecules are prevented from rapid release due to covalent bonding to the polymeric carrier.

The vaccine composition of the invention does not require the coupling of the antigen and/or adjuvant directly to single polymer chains up-front to particle formation, thereby fully retaining the initial properties of the polymers used, such as thermo-sensitive properties and/or the ease of antigen and/or adjuvant loaded micelle formation. The use of a fixed type of polymer, for example thermo-sensitive biodegradable block copolymers, provides a broadly applicable platform technology that allows a rapid and easy change/optimization of the composition of the antigen and/or adjuvant loaded devices.

The vaccine composition of the present invention is applicable to all antigen and/or adjuvant that are capable of non-covalently interacting with polymer chains which are capable of forming polymeric carriers after cross-linking. In the aqueous phase, the polymer chains (before the cross-linking step) preferably assemble in a certain structure, or at least in polymer chain-rich domains; and the antigen and/or adjuvant localise in these assemblies. All types of physical interactions are possible (see below).

The only further requirement is that the antigen and/or adjuvant contains a moiety (or can be modified with a reactive substituent) that is capable to react with a moiety of the polymer chains that form the basis of the polymeric particle.

In a preferred embodiment, the antigen and/or adjuvant is provided with a linker molecule, preferably a degradable linker.

By covalent entrapment of the antigen and/or adjuvant in the core of the carrier, such as in the micellar core, the antigen and/or adjuvant does not come free at the beginning, it does not have a "burst release". It will benefit from the prolonged residence and/or blood circulation of the cross-linked carrier in the body, thereby acting as a depot on the injection site and/or in the blood stream while simultaneously, this can lead to elevated antigen and/or adjuvant concentrations in the target tissue e.g. tumour, lymph node, or inflamed tissue. In addition, the vaccine composition of the present invention may obtain a long term product stability by subjecting these to lyophilisation. For example, vaccine compositions according to the present invention comprising antigen and/or adjuvant-loaded particles may easily be freeze-dried and subsequently suspended without loss of morphology; as dry powder, a long shelf life is obtained. This is advantageous as especially in developing countries, vaccine compositions that do not need refrigeration, and/or are a dry powder are preferred.

Hence, the present invention concerns a vaccine composition wherein the particle starts with the non-covalent entrapment of antigens and/or adjuvants in polymeric carriers in an aqueous environment, whereby the polymer chains of the polymeric carrier contain at least one reactive moiety. This non-covalent entrapment is followed by a simultaneous crosslinking reaction between the antigen and/or adjuvant and the polymer chains and between the polymer chains themselves, thereby forming an intertwined network. In a preferred embodiment, a further conjugation step is performed, to conjugate antigen and/or adjuvants and/or targeting ligands to the surface of the particle.

The resulting antigen and/or adjuvant-loaded polymeric devices, such as micelles, do not display a premature release of antigens and/or adjuvant (burst release), but demonstrate a prolonged residence at site of injection and/or blood circulation e.g. upon parenteral administration. In a preferred embodiment, the antigen and/or adjuvant comprises a suitable linker that allows sustained release of entrapped compounds in time, preferably each with its own specific release rate. This may result for instance in a (greatly) enhanced dendritic cell (DC) targeting, and accumulation in the lymph node, thereby activating the immune system.

In a preferred embodiment, the antigen and/or adjuvant is entrapped via a linker to the polymer matrix, preferably a degradable linker and more preferably a biodegradable linker. Such a system allows a pulsatile or constant release of the adjuvant and/or antigen. Controlled release of the antigen and/or adjuvant from the carrier is accomplished by cleavage of the, preferably degradable, linker or linking group between the antigen and/or adjuvant, and the polymeric carrier under physiological conditions, or by local environmental triggers or external stimuli as explained and elaborated, herein-below. In addition, the entrapment prevents exposure of blood to toxic high antigen and/or adjuvant peak levels that would otherwise be present immediately after intravenous administrations of free antigens and/or adjuvants, or in non-covalently entrapped antigens and/or adjuvants. More importantly, by preventing migration of the system to normal tissues, acute toxic effects may be diminished. The other way around, the antigen and/or adjuvant are fully protected from the environment by confinement in the formed three-dimensional network of the cross-linked polymer carrier, such as a cross-linked micellar core, thereby preventing a premature degradation and/or clearance. These unique aspects deliver the antigen and/or adjuvant at the right place and time, and at an anticipated efficacious dose.

Alternatively, in a preferred embodiment of the invention and embodiments thereof, adjuvants and/or antigens on the surface of the particles may not need to be released, as they will be available for the immune system by being present on the outer surface of the particles.

The stepwise method of making the particle of the vaccine composition of the invention comprises two essential consecutive steps.

In the first step, a cross-linkable polymer and a antigen and/or adjuvant are mixed in an aqueous environment. This is preferably achieved by adding the antigen and/or adjuvant, optionally in a suitable solvent that preferably is water or a water miscible solvent such as a lower alcohol like ethanol, tetrahydrofuran, or dimethylsulphoxide to an aqueous polymer solution or dispersion. The polymer present and the antigen and/or adjuvant are selected so that the polymer and the antigen and/or adjuvant will be in intimate contact, and in a preferred embodiment, the antigen and/or adjuvant is in contact with the polymer chains. Said in other words, in the first step physical, non-covalent interactions between the polymer chains and the antigen and/or adjuvant result in the selective localisation of compounds in specific regions of a polymeric device.

As a result of the first step, the molecules forming the antigen and/or adjuvant are non-covalently entrapped in and between the polymer chains in solution. In the present description and the appending claims, the concept of "non-covalent interaction" means any interaction which is not covalent, i.e. any bonding between atoms or bonds which bonding does not involve the sharing of electron pairs. Examples of non-covalent interaction are hydrophobic, aromatic, hydrogen bonding, electrostatic, stereocomplex, and metal-ion interactions.

In the second or third essential step of the method of making the particle of the vaccine composition of the invention, following the first step, the non-covalently entrapped antigens and/or adjuvants are covalently coupled to the newly forming/formed polymer network. That is, a reaction is carried out, wherein the polymer chains are cross-linked. This can occur both inter- and intramolecularly, but the intermolecular cross-links are clearly preferred and any steps that favour intermolecular cross-linking are preferred embodiments of the presently claimed process. Simultaneously with the cross-linking step, the reactive moieties of the antigen and/or adjuvant are also co-cross-linked to the polymer chains and an intertwined network of the polymers and antigen and/or adjuvant is formed. Suitably, the polymer comprises more than one reactive group and may react with more than one antigen and/or adjuvant. In a preferred embodiment, the polymer comprises different reactive groups that are capable of reacting with each other, thereby forming a 3-D network of the polymer and the antigen/adjuvant. Polymers that comprise two or more different reactive groups may be used. In addition, the different reactive groups may be present on different polymers.

This step may require initiators and/or catalysts, but also physical circumstances may lead to the reactions forming cross-links and conjugates. In case initiators and/or catalysts are required, these may be added to the polymer solution together with the antigens and/or adjuvants, but can also be added to the reaction system at an earlier or later stage. In a preferred embodiment the initiator is not a free radical Free radicals may react with the antigen and/or adjuvant itself thereby altering their properties. This is especially true for sensitive amino acids, such as tyrosine and/or tryptophan. Aromatic side chains or sulfhydryl groups are thereby usually considered to be the most reactive parts of amino acids with respect to free radicals.

Suitable amounts of antigen and/or adjuvant are amounts of 0.1-30 wt. %, preferably 0.5-15 wt. %, such as amounts of 1-10 wt. % drawn to the weight of polymer+antigens and/or adjuvants. Since the degree of incorporation of antigen and/or adjuvant may be as high as 95-100%, similar amounts may be incorporated in the formed 3D-network.

According to a preferred method of the present invention, amphiphilic polymers may be fully dissolved in a solvent.

Antigens and/or adjuvants may be present in the solvent or may be added after the dissolution of said polymers or even upon self-assembly into loose micelles, and the antigens and/or adjuvants will form a general distribution over the polymer or micellar solution;

then, this system may be subjected to a change of certain circumstances (e.g. temperature, pH, solvent) leading to a situation that at least parts of the polymers display a different behaviour than other parts of the polymers and clustering takes place;

due to the physical properties of the antigen and/or adjuvant, these antigen and/or adjuvant localise in certain regions of the newly formed clustered polymeric solution;

after this localisation, cross-linking takes place to fixate the antigen and/or adjuvant in their preferred regions.

In a preferred embodiment of the method of the invention, thermosensitive block copolymers are used. For example, the antigen and/or adjuvant is mixed in an aqueous environment, wherein also a non-cross-linked thermosensitive block copolymer is present at a temperature lower than its Lower Critical Solution Temperature (LCST) or lower than its critical micelle formation temperature (CMT). At any temperature below this LCST, the system is in solution; at any temperature below this CMT, micelle formation does not occur. However, by heating such systems, particles or micelles are formed thereby entrapping the antigen and/or adjuvant in their hydrophobic core. Alternatively, empty micelles are formed in step (i) without the antigen and/or adjuvant. Subsequently an antigen and/or adjuvant solution is added to the empty micelles. Next, the cross-linking reaction that forms the intertwined micellar network in the core is also carried out at a temperature higher than the LCST or the CMT. This cross-linking reaction can be accelerated by the addition of an initiator/and or catalyst, either prior to heating of the polymer solution or after formation of the non-cross-linked particles or micelles. The method of forming first the nanoparticles and then adding the antigen and/or adjuvant before the crosslinking may be very suitable for peptides.

In another preferred embodiment of the method of the invention and embodiments thereof, the polymers do not need harsh conditions for making the particles. Suitably, the formation of the particles is without organic solvents and/or other chemicals or solvents that may harm the adjuvant and/or antigen. Suitable polymer chains that can be used in the present invention are, e.g., thermo-sensitive block copolymers. Particularly, copolymers based on PEG-b-poly(N-hydroxyalkyl methacrylamide-oligolactates) with partially methacrylated oligolactate units are preferred. Various other (meth)acrylamide esters can be used to construct the thermosensitive block, e.g. esters, and preferably (oligo)lactate esters, of HPMAm (hydroxypropyl methacrylamide) or HEMAm (hydroxyethylmethacrylamide), and N-(meth)

acryloyl amino acid esters. Preferred thermo-sensitive block copolymers are derived from monomers containing functional groups which may be modified by methacrylate groups, such as HPMAm-lactate polymers.

Other types of functional thermosensitive (co)polymers, which can be used, are hydrophobic ally modified poly(N-hydroxyalkyl)(meth)acrylamides, copolymer compositions of N-isopropylacrylamide (NIPAAm) with monomers containing reactive functional groups (e.g., acidic acrylamides and other moieties such as N-acryloxysuccinimide) or similar copolymers of poly(alkyl) 2-oxazalines, etc.

Further preferred thermo sensitive groups can be based on NIPAAm and/or alkyl-2-oxaxolines, which monomers may be reacted with monomers containing a reactive functional group such as (meth)acrylamides or (meth)acrylates containing hydroxyl, carboxyl, amine or succinimide groups.

Suitable thermo-sensitive polymers are described in U.S. Pat. No. 7,425,581 and in EP-A-1 776 400.

However, also other types of amphiphilic block copolymers or ionic micelles that are not necessarily thermosensitive and contain or can be modified with cross-linkable reactive groups, may be used. In such cases state-of-the-art methods can be used to form the particles and/or micelles, such as direct dissolution, dialysis, salting-out and solvent-evaporation.

These other types of polymers that conform polymer-rich phases in water (e.g. due to hydrophobic interactions or ionic interactions) and that contain reactive moieties or contain moieties that can be used to couple reactive moieties, e.g. PEG-PLA-methacrylate (e.g. as described in detail in Kim et al., Polym. Adv. Technol., 10 (1999), 647-654), methacrylated PLA-PEG-PLA (e.g. as described by Lee et al. in Macromol. Biosci. 6 (2006) 846-854), methacrylated PEG-poly caprolactone (e.g. as described by Hu et al. in Macromol. Biosci. 9 (2009), 456-463), as well as other reactive moieties containing (block co)polymers based on poly lactic acid, poly lactic acid glycolic acid, and/or poly caprolactones.

In addition, polymers capable of forming micelles because of ionic interactions may be used, such as block ionomer complexes of poly(ethylene oxide)-b-polymethacrylic acid copolymers and divalent metal cations (e.g. as described by Kim et al. in J. Control. Rel. 138 (2009) 197-204, and by Bontha et al. in J. Control. Rel. 114 (2006) 163-174) polyionic complexes based on block copolymers of poly(ethylene glycol) and poly(amino acid) (e.g. as taught in Lee et al., Angew. Chem 121 (2009) 5413-4516; in Nishiyama et al. in Cancer Res. 63 (2003), 8977-8983, or in Miyata et al., J. Control. Rel. 109 (2005) 15-23.

In general, all polymers that are able to create different subphases in a suitable solvent system can be used, together with an adjuvant and/or antigen that can localize selectively in such subphases.

The polymer chains and the antigen and/or adjuvant contain or may be modified such that these contain reactive moieties. The polymers used should contain a sufficiently high number of reactive substituents capable of cross-linking and reacting with the reactive groups of the adjuvant and/or antigen. Suitable results are obtained when for instance 10-15%, 15-20%, 20-25%, 25-30%, 30-35%, 35-40%, 40-45%, or 45-50% of the monomer units of the polymer have a reactive substituent; however also up to 100% of the monomer units may be derivatised with reactive substituents. For example 50%, 55%, 60%, 65%, 70%, 75%, 80%, 85%, 90% or 95% of the monomer units may be derivatised with reactive substituents. Also 1-10%, 2-8%, 3-7%, 4-6%, and 2-5% of the monomer units may be derivatised with reactive substituents.

Also the adjuvant and/or antigen have reactive substituents that are capable of crosslinking, preferably to the polymers so that an adjuvant/antigen-polymer matrix is formed. In a preferred embodiment of the present invention and embodiments thereof, the adjuvant and/or antigen have at least one reactive moiety or substituent that is capable of cross-linking. Preferably, more than 1, such as 2, 3, 4, or 5 reactive moieties are present on the adjuvant and/or antigen. It should be understood that larger molecules may have more reactive moieties than smaller molecule, and it thus the amount of reactive moieties largely depends on the size of the adjuvant and/or antigen. Antigens and adjuvants may be large biomolecules and hence may contain more than 5, or even more than 10, or even more than 15, or even more than 20 or even more than 25 reactive moieties. In the context of the present invention, reactive moiety, reactive substituent, and reactive group are used interchangeably and all mean a group that is capable of an action such as cross-linking and linking to another molecule.

The release rate of the antigen and/or adjuvant can easily be controlled by using different type of linkers to conjugate the reactive moiety to the antigens and/or adjuvants. Suitable types of well-known degradable linker molecules include but are not limited to esters, carbonates, imines, carbamates, succinate or ortho (oxime) esters, ketals, acetals, hydrazone, and enzymatically degradable linkers (e.g. peptides) or a combination of these. In addition, all kinds of well-known stimuli sensitive linkers, such as photo-/temperature-/ultrasound-sensitive and other linkers can also be used. When modifying antigens and/or adjuvants, one takes care of the type of conjugation such that upon release, only the antigen and/or adjuvant is released and no derivatives that may have other activities, as to assure its full activity. By using a biodegradable linkage, the original antigen and/or adjuvant, will be released according to a specific controlled release profile and subsequently exert its activity and especially its immunogenic or stimulating effect.

Vaccine composition of the present invention are polymer carriers, such as micelles, nanoparticles, microspheres, hydrogels and other types of polymer carriers or devices comprising entrapped or otherwise incorporated antigens and/or adjuvants for controlled release, such as devices with a coating with entrapped antigens and/adjuvants.

As said, in the second (or third) essential step of the method of the invention, cross-linking and conjugation is effected. Free radical initiators may not be suitable for use with an antigen and/or an adjuvant because they may react to the antigen and/or adjuvant itself, thereby altering its properties. The crosslinking may therefore be performed without a free-radical. Preferable the crosslinking is non-propagating, e.g. forming only 1 bond per reaction. A suitable cross-linking can be via Michael-addition (Censi et al J. Control Rel 148 (2010) e28-e29). Suitable crosslinking according to the invention is cross linking resulting in a bond selected from the group consisting of ester, hydrazine, amide, Schiff-base, imine, acetal bonds and similar biodegradable bonds, including any potential corresponding derivatives of them. Suitable crosslinking according to the invention is cross linking with a reactive moiety selected from alcohol, acid, carboxyl, hydroxyl, amine, hydrazine, etc. Also photopolymerisation is suitable (Censi et al J. Control Rel 140 (2009) 230-236). The reactive moieties may be present in the polymer chain, and/or in the antigen and/or adjuvant and/or on a linking molecule. In a preferred embodiment the linker or polymer comprises more than 1 reactive moiety so as to form multiple bond. A suitable example is a star-like structures, e.g. 8-arm COOH-derivatised-PEG that may react with OH-containing polymers and/or antigens and/or adjuvants. Without any radical, a dense 3D network may be formed while protecting sensitive compounds.

In a preferred embodiment the reaction conditions are fairly mild and take place in aqueous environment, to protect the integrity of the antigen and/or adjuvant. Preferably the crosslinking results in biodegradable linkages.

When the adjuvant and/or antigen is entrapped via a degradable linker, a constant release of the therapeutically active compound is assured. Controlled release of the adjuvant and/or antigen from the carrier is accomplished by cleavage of the, preferably degradable, linker or linking group between the active ingredient, such as adjuvant and/or antigen, and the polymeric carrier under physiological conditions, or by local environmental triggers or external stimuli as explained and elaborated, herein-below. A suitable example of degradable linker may be found in WO2012/039602 which is incorporated by reference.

Such a linker can be exemplified by the following formula:

HOQ-$(C_nH_{2n})$—S($R_1$)($R_2$)—$(C_mH_{2m})$—$CH_2$-A, wherein n and m are integers from 0 to 20, and preferably from 1 to 10. In preferred embodiments, n is an integer from 1-5, more preferably from 1-3; and m is an integer from 1-7; more preferably from 1-5;

wherein $R_1$ and $R_2$ are independently from each other selected from an electron lone pair, an oxygen moiety, such as =O, a nitrogen moiety, such as =N—$R_x$, wherein $R_x$ is a homo- or heterogeneous group of atoms, and preferably, independently, a straight or branched $C_1$-$C_6$ alkyl, a straight or branched $C_1$-$C_6$ alkenyl, which alkyl or alkenyl group may optionally be substituted by one or more halogen groups, hydroxyl groups, amino or substituted amino groups, carboxylic acid groups, nitro groups or cyano groups; or aromatic groups, and preferably a phenyl group optionally be substituted by one or more of the substituents mentioned for the alkyl and alkenyl groups; or a halogen group, a hydroxyl group, an amino group, or a substituted amino group (the substituents being one or two $C_1$-$C_3$ alkyl groups), a carboxylic acid group, a nitro group, or a cyano group;

wherein A is a conjunction moiety; and wherein Q is a direct bond, a C=O, a C=NH or C=$NR_p$ group, wherein $R_p$ is a $C_1$-$C_3$ alkyl. In this formula the HO-Q group can be replaced by a H$R_9$N-Q group, wherein $R_9$ can either be a hydrogen atom or a $C_1$-$C_3$ alkyl group.

In the following preferred linker formula, the HO-Q group is a carboxylic acid group and the conjugation moiety A is a polymerisable methacrylate, which moieties are also exemplified in the working examples herein-below:

carboxylic acid        conjugation moiety, in this example a polymerisable methacrylate It should be understood that the above example is not limited and that for example the methacrylate group may be substituted with any polymerisable group as described in the specification. Suitable conjugation groups are polymerisable moieties of the formula —PL-$R_v$C=CR=$R_w$, wherein —PL- is a linking group such as an —O—, a —NH—, a substituted —N—, the substituent being a $C_1$-$C_3$ alkyl, an —O—C(O)—, an —O—(C(O))$_r$—$C_6H_{26}$—, wherein r is 0 or 1, and b is an integer from 1 to 6; and $R_u$, $R_v$ and $R_w$, independently, represent a hydrogen atom or a $C_1$-$C_3$ group.

In a preferred embodiment, an additional step comprises the conjugation of one or more compounds to the outer surface of the particle. In the conjugation step, the adjuvant, antigen and/or targeting compound is conjugated to the reactive moieties of the polymer. Suitably, the polymer comprises a reactive moiety that may interact with an adjuvant, antigen and/or targeting compound after the crosslinking step. In a preferred embodiment, the end terminal of the polymer comprises a reactive moiety that may interact with a antigen, adjuvant and/or targeting compound that may be suitably derivatised. The reactive moiety of the end terminal of the polymer, ensures that the physical-chemical properties of the polymer are unchanged, while an additional functionality is employed. For particles wherein the surface is not further modified, the polymer has a non/reactive moiety, such an methoxy, on the end terminal. A suitable polymer is X-PEG-b-HPMAmLacx, whereby X can be any reactive moiety that can interact with an (Y-derivatised) compound, resulting in a stable or biodegradable bond. The latter is dependent on the type of compound use, i.e. when its biological activity is negatively affected by the conjugation, it might require a biodegradable bond whereas for internalizing ligands, a stable bond is required to assure integer intracellular uptake of the entire particle.

In a preferred embodiment, the percentage if the X-polymer can be between 0 and 100%, in a preferred setting between 0-50%, more preferred 0-20%, and is a good control for the % of reactive moieties that can be conjugated to the surface.

In this way, the particles not only entrap antigens and/or adjuvant, but really target the particles to antigen presenting cells (APCs) that are required for eliciting the desired type of immuneresponse. In a preferred embodiment, the adjuvant, antigen and/or targeting compound on the surface of the particle is utilised with a linker, preferably a degradable linker. For large antigens and/or adjuvants, that do not fit inside the particle and/or are not suitable to be entrapped inside the particle, conjugation on the surface of the particle may be very suitable. For nucleic acids, conjugation to the outside surface, preferably via a degradable linker, is very suitable.

In a preferred embodiment targeting compounds are conjugated to the surface of the particles. The targeting compounds may suitably target dendritic cells (DCs). The human DCs are identified by over expression of human leukocyte antigen (HLA) DR (major histocompatibility complex class II). In addition, the specific markers for identifying the myeloid DCs include CD11c+, CD1a+, BDCA-1+, BDCA-3+, HLA-DR+ whereas for the plamacytoid DCs they are CD11c−, HLADR+, BDCA-2+ and CD123+. In a preferred embodiment, the targeting compound binds or is able to bind to CD11, CD11a, BDCA-1, BDCA-3, HLA-DR, BDCA-2 and CD123, toll-like receptors (TLR), C-type lectin receptors (CLR), and nod-like receptors (NLR). Suitable targeting compounds are presented in table 1.

TABLE 1 targeting compounds:

| Targeting receptor | Targeting compound |
|---|---|
| TLR 1/2 | $Pam_3CAG$ |
| TLR 2/6 | $Pam_2CAG$ |
| TLR 3 | Poly (I:C) |
| TLR 4 | LPS |
| TLR 4 | Lipid A |
| TLR 4 | MPLA |
| TLR 5 | Flagelin |
| TLR 7 | 3M019 |
| TLR 9 | Plasmid DNA |
| TLR 9 | CpG ODN |
| Mincle | TDM |
| Dectin-1 | B-glucan |
| NOD2 | MDP |

In addition, suitable targeting compounds for cancer vaccination may be selected from the group consisting of mannose/mannan, ligands for the Fc receptors for each immunoglobulin class, CD11c/CD18 and DEC 205 receptor targets, DC-SIGN receptor targets. A skilled person is well aware of suitable targeting compounds for desired target cells and is able to select the desired targeting compounds. In the context of this invention, targeting ligand, targeting agent, targeting compound or targeting group are used interchangeably, and all mean a compound that is able to target a specific cell or specific tissue.

In a preferred embodiment the antigen is a peptide or (part of) a protein. According to the present invention, a peptide is a polymer of amino acids linked by peptide bonds. They have the same peptide bonds as those in proteins, but are commonly shorter in length. The shortest peptides are dipeptides, consisting of two amino acids joined by a single peptide bond. According to the invention a peptide may be up to 1000 amino acids long, e.g. between 10 and 500 amino acids, preferably between 12 and 450 amino acids, more preferably between 15 and 400 amino acids, more preferably between 17 and 375 amino acids, more preferably between 20 and 350 amino acids, more preferably between 22 and 300 amino acids, more preferably between 25 and 250 amino acids, more preferably between 27 and 225 amino acids, more preferably between 30 and 200 amino acids, more preferably between 33 and 175 amino acids, more preferably between 35 and 150 amino acids, more preferably between 37 and 150 amino acids, more preferably between 40 and 125 amino acids, more preferably between 45 and 100 amino acids, more preferably between 50 and 85 amino acids, more preferably between 55 and 75 amino acids and most preferably between 60 and 70 amino acids. Suitable peptides comprise 3 to 100 amino acids, more preferably 3 to 90 amino acids, more preferably 3 to 80 amino acids and most preferable from 3 to 70 amino acids. Peptides have an amino end and a carboxyl end, unless they are cyclic peptides. It is to be understood that polypeptides, oligopeptides and even proteins are envisioned under the term peptides according to the present invention.

It should be understood that a mixture of an antigen and an adjuvant may be entrapped in a particle according to the present invention. Preferably, the antigen and/or adjuvants should be of a nature such that these tend to interact in a physical non-covalent manner with the polymer chains of the polymers described herein-above. In a preferred embodiment, the invention is especially useful for encapsulation of hydrophobic compounds, preferably using thermosensitive polymers.

Nanoparticle-based vaccine recapitulates the immunogenicity of live viral vaccines and may induce long-lived protection, possibly as a consequence of persistent antigen-adjuvant complexes.

In the vaccine composition of the present invention and/or embodiments thereof, the antigen may be any antigen. In the case the antigen is a nucleic acid, the antigen is preferably conjugated to the surface of the particle. In a preferred embodiments, the antigen may be selected form the group of chemicals, bacteria bacterialexcretions such as toxins, LPS, bacteriophages, mycobacterial antigens, ovalbumin, viruses, or any part thereof. Suitably the antigen is a surface protein, or part thereof from bacteria, viruses, bacteriophages, and/or mycobacteria. Suitable examples are antigens from diphtheria toxoid, diphtheria CRM-197, human papillomavirus, malaria virus antigens, west Nile virus, (recombinant) hepatitis A or B (surface or core antigens), cytomegalovirus, HIV, anthrax, rabies, candidiasis, influenza (various type), e.g. subunit like hemagglutinin, and neuraminidase, ortuberculosis, e.g. Ad35-vectored tuberculosis (TB) AERAS-402. The skilled person will be able to select the appropriate antigen based on the type of vaccine and route of administration.

In a preferred embodiment of the present invention and/or embodiments thereof, the particle may comprise more than one antigen. More than one antigen of the same disease agent may be used, and/or antigens from different disease agents may be used for e.g. multivaccines.

The vaccine composition of the present invention and/or embodiments thereof, preferably comprises an adjuvant. Known adjuvants are a very diverse set of compounds ranging from bacterial toxins, particulates, plant derivatives and pathogen-associated molecular patterns (PAMPs). A useful database for potential adjuvants is Vaxjo and may be found on http://www.violinet.org/. The database Vaxjo is hereby incorporated by reference.

Suitable examples of adjuvants may be selected from the group consisting of cobalt oxide, aluminum hydroxide hydrate, aluminumphosphate, potassiumaluminumsulfate, inactivated and dried mycobacteria (usually *M. tuberculosis*) (part of Freund's adjuvant), CT: Cholera toxin; including CTB: B subunit of cholera toxin, LT: *Escherichia coli* heat-labile toxin, Imiquimod, Montanide, including Montanide™ ISA51, MF59™: squalene oil, dispersed in the form of 160 nm droplets, conveniently stabilized with a mixture of a high HLB (polysorbate 80) and a low HLB surfactant (sorbitan trioleate), AS02™: squalene and two hydrophobic immune adjuvants, MPL1TM, a synthetic derivative of LPS, and QS-21, a purified saponin plant extract. Preferred adjuvants are alum (aluminium hydroxide), squalene or MF59.

In a preferred embodiment of the present invention and/or embodiments thereof, the particle may comprise more than one adjuvant.

The vaccine composition of the present invention and/or embodiment thereof may suitably be used for therapeutic and/or prophylactic purposes. Examples of fields of use may be oncology, tuberculosis, bacterial infections, diphtheria, hepatitis B, influenza, HIV, HCV, flavivirus, west-nile virus, dengue virus. It is understood that any kind of indication may be possible, and that the present invention is not limited to the examples indicated above.

Suitably, the invention and/or embodiments thereof is related to the use of a vaccine composition in a prophylactic manner. Suitable, the present invention is directed to the use of vaccine composition of the present invention and/or embodiments thereof for immunisation against a disease.

Furthermore, the vaccine composition of the present invention and/or embodiments thereof, is for use as a medicine. In a preferred embodiment, the vaccine composition of the present invention and/or embodiments thereof, is for use against a disease. The invention is also related to a method of treatment using and/or administering to a subject the vaccine composition of the invention.

In a preferred embodiment the disease is selected form the group consisting of cancer, infection, opthalmological diseases, viral infection, bacterial infection, fungal infection, mucoplasma infection, parasite infection, inflammation, Dermatological diseases, Cardiovascular diseases, diseases of the central nerve system, auto-immune disease, proliferative diseases, arthritis, psychotic diseases, psoriasis, diabetes, metabolic disorders, lung diseases, respiratory diseases, pulmonary diseases, COPD, diseases of the muscoskeletal system, emphysema, edema, hormonal diseases. More specifically the vaccine composition of the present invention and/or embodiments thereof is suitable for treatment of diseases including but not limited to diseases selected from the group consisting of spinal cord injuries, heart attacks, ischaemi, arthritis, fungal infections, post operative pain, pain, non-small cell lung cancer (or cancer-small cell lung, bladder, non-Hodgkin's lymphoma, general gastrointestinal, colorectal, head and neck, breast, general solid), acute lymphocytic and acute myelogenous leukemia, breast cancer, brain cancer, general leukaemia, liver cancer, pancreas cancer, colorectal cancer, cervical cancer, general lymphoma, ovarian cancer, squamous cell cancer, general lung cancer, pancreatic cancer, bladder cancer, renal cancer, liver cancer, small cell lung cancer, stomach cancer, Hodgkin's lymphoma, non-small cell lung cancer, oesophageal cancer, adrenal cancer, melanoma, Myelodysplastic syndrome, hairy cell leukaemia, general skin, bladder, head and neck, non-small cell lung, oesophageal, ovarian, melanoma, leiomyosarcoma, biliary, breast, prostate, systemic Lupus erythematosus, mesothelioma, and/or general sarcoma.

Moreover, the vaccine composition of the present invention and/or embodiments thereof is suitable for treatment of disease including but not limited to a disease selected from the group consisting of diseases to the eyes, infectious diseases, inflammatory diseases, cancer, cardiovascular diseases, diseases from the central nervous system, autoimmune disease, and/or other diseases such as diabetes insipidus, polyuria, polydipsia, post-surgery pain and/or spinal cord injuries.

Infectious diseases may be selected from the group including bacterial infections including gram-negative infections, infections of skin, and/or fungal infections.

Inflammatory diseases may be selected from the group including rheumatoid arthritis, diabetes type I, diabetes type II, appendicitis, bursitis, colitis, cystitis, dermatitis, meningitis, phlebitis, rhinitis, tendonitis, tonsillitis, and/or vasculitis.

Cancer may be selected from the group including hormone sensitive prostate cancer, hormone sensitive breast cancer, non-small cell lung cancer, small cell lung cancer, bladder cancer, non-Hodgkin's lymphoma, general gastrointestinal cancer, colorectal cancer, head and neck cancer, breast cancer, acute lymphocytic leukaemia, acute myelogenous leukaemia breast cancer, brain cancer, leukaemia, liver cancer, testicular cancer, small cell lung carcinoma, ovarian cancer cervical cancer, squamous cell cancer, pancreatic cancer, renal cancer, stomach cancer, Hodgkin's lymphoma, oesophageal cancer, adrenal cancer, melanoma, Myelodysplastic syndrome, hairy cell leukaemia skin cancer, leiomyosarcoma, prostate cancer, systemic Lupus erythematosus, mesothelioma, and/or sarcoma.

Diseases to the eyes may be selected from the group including macular degeneration, acute postoperative endophthalmitis macular edema, and/or cataract.

Cardiovascular diseases may be selected from the group including vasoconstriction, coronary heart disease, ischaemic heart disease, coronary artery disease, cardiomyopathy, hypertensive heart disease, heart failure, cor pulmonale, cardiac dysrhythmias, inflammatory heart disease, endocarditis, inflammatory cardiomegaly, myocarditis, valvular heart disease, stroke and cerebrovascular disease, peripheral arterial disease, hypertension, and/or atherosclerosis.

Diseases from the central nervous system may be selected from the group including encephalitis, poliomyelitis, neurodegenerative diseases such as Alzheimer's disease, amyotrophic lateral sclerosis, autoimmune and inflammatory diseases such as multiple sclerosis or acute disseminated encephalomyelitis, and genetic disorders such as Krabbe's disease, Huntington's disease, and/or adrenoleukodystrophy.

Autoimmune diseases may be selected from the group including Acute disseminated encephalomyelitis (ADEM), Addison's disease, Agammaglobulinemia, Alopecia areata, Amyotrophic Lateral Sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic recurrent multifocal osteomyelitis, Chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Drug-induced lupus, Discoid lupus erythematosus, Eczema, Endometriosis, Enthesitis-related arthritis, Eosinophilic fasciitis, Eosinophilic gastroenteritis, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Giant cell arteritis, Glomerulonephritis, Goodpasture's syndrome, Graves' disease, Guillain-Barré syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura (See Autoimmune thrombocytopenic purpura), IgA nephropathy, Inclusion body myositis, Chronic inflammatory demyelinating polyneuropathy, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lou Gehrig's disease (Also Amyotrophic lateral sclerosis), Lupoid hepatitis aka Autoimmune hepatitis, Lupus erythematosus, Majeed syndrome, Meniere's disease, Microscopic polyangiitis, Miller-Fisher syndrome see Guillain-Barre Syndrome, Mixed connective tissue disease, Morphea, Mucha-Habermann disease aka *Pityriasis* lichenoides et varioliformis *acuta*, Multiple sclerosis, Myasthenia gravis, Myositis, Narcolepsy[46][47], Neuromyelitis optica (also Devic's disease), Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with *streptococcus*), Paraneoplastic cerebellar degeneration, Paroxysmal nocturnal hemoglobinuria (PNH), Parry Romberg syndrome, Parsonage-Turner syndrome, Pars planitis, Pemphigus vulgaris, Pernicious anaemia, Perivenous encephalomyelitis, POEMS syndrome, Polyarteritis *nodosa*, Polymyalgia rheumatica, Polymyositis, Primary biliary cirrhosis, Primary sclerosing cholangitis, Progressive inflammatory neuropathy, Psoriasis, Psoriatic arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatic fever, Sarcoidosis, Schizophrenia, Schmidt syndrome another form of APS, Schnitzler syndrome, Scleritis, Scleroderma, Serum Sickness, Sjögren's syndrome, Spondyloarthropathy, Still's disease see Juvenile Rheumatoid Arthritis, Stiff person syndrome, Subacute bacterial endocarditis (SBE), Susac's syndrome, Sweet's syndrome, Sydenham chorea see PANDAS, Sympathetic ophthalmia, Systemic lupus erythematosis see Lupus erythematosis, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), Undifferentiated connective tissue disease different from Mixed connective tissue disease, Undifferentiated spondyloarthropathy, Urticarial vasculitis, Vasculitis, Vitiligo, and/or Wegener's granulomatosis.

Other diseases may be selected from the group including diabetes insipidus, polyuria, and/or polydipsia, pruritus post-surgery pain and/or spinal cord injury including paraplegia.

The vaccine composition of the present invention and/or embodiment thereof may suitably used for several routes of administration. Suitable routes are parenteral, intravenous (i.v.), subcutaneous (s.c.), intramuscular, intralymphatic, intraperitoneal, oral, including buccal, and sublingual, mucosal develivery, such as intra-nasal, and pulmonary, dermal such as topical, transdermal, transcutaneous.

For the purpose of clarity and a concise description features are described herein as part of the same or separate embodiments, however, it will be appreciated that the scope of the invention may include embodiments having combinations of all or some of the features described.

EXPERIMENTAL DATA

By way of example, the formation of a specific embodiment of the method of the present invention is described. The examples are in no way to be construed as limiting to the invention.

Example 1 Leuprolide Covalently Entrapped in Crosslinked Nanoparticles

In this example one starts from copolymers based on thermo-sensitive PEG-b-poly(N-hydroxyalkyl methacrylamide-oligolactates) with partially methacrylated oligolactate units. Leuprolide is derivatised with a reactive moiety that is attached to a sulfoxide-methacrylate (L2 in WO2012/039602) which is a degradable linker. An aqueous solution of said thermo-sensitive block copolymers is subsequently mixed with a small amount of a concentrated solution (typically 10:1 volume ratio) of leuprolide in tetrahydrofuran at a temperature below the polymers CMT, i.e. that does not allow micelle formation, i.e. 0 degrees C. Then, an initiator/catalyst solution (potassium persulphate (KPS)—N,N,N',N'-tetramethylethylenediamine (TEMED) is added, immediately followed by rapid heating till above the critical micelle formation temperature (CMT), i.e. 20 degrees celsius. This results in the formation of monodisperse polymeric micelles (size around 70 nm, PDI less than 0.2) where the leuprolide is non covalently localised in the hydrophobic core. After micelle formation, a nitrogen atmosphere is created. Thereby, the initiator radicals induce polymerisation of the methacrylated polymers and the polymerisable leuprolide having the reactive moiety. This cross-linking process results in the formation of an intertwined network and fixates the leuprolide covalently inside the micellar core, without affecting the micellar size or uniformity.

Thus, the leuprolide is covalently entrapped in the cross-linked micelles. The leuprolide is released by hydrolysis and the micelles swell in a physiological environment by hydration after (partial) hydrolysis of the unmodified oligolactate units. Thus the release of the leuprolide and degradation of the micelles occurs parallel. This cleavage can also be the result of local environmental triggers or external stimuli.

The composition and/or method of the invention is not limited to the use of polymers that can form micelles. It also allows for the non-covalent entrapment and subsequent covalent cross-linking of (drug) molecules in polymeric nanoparticles, microspheres, hydrogels or coatings.

The vaccine composition of the present invention with antigen and/or adjuvant loaded particles are flexible systems that assure the rational design of the antigen and/or adjuvant-loaded nanoparticle as to target specific cells and/or indications, e.g. mucus-adhesive particle for sustained release of therapeutic or vaccination purposes (nasal, pulmonary, or gastro-intestinal tract, in case of vaccination with virus like particle), sustained release of antigens and/adjuvants loaded nanoparticle.

Example 2 Leuprolide and Degradable Linkers

Figure 1:
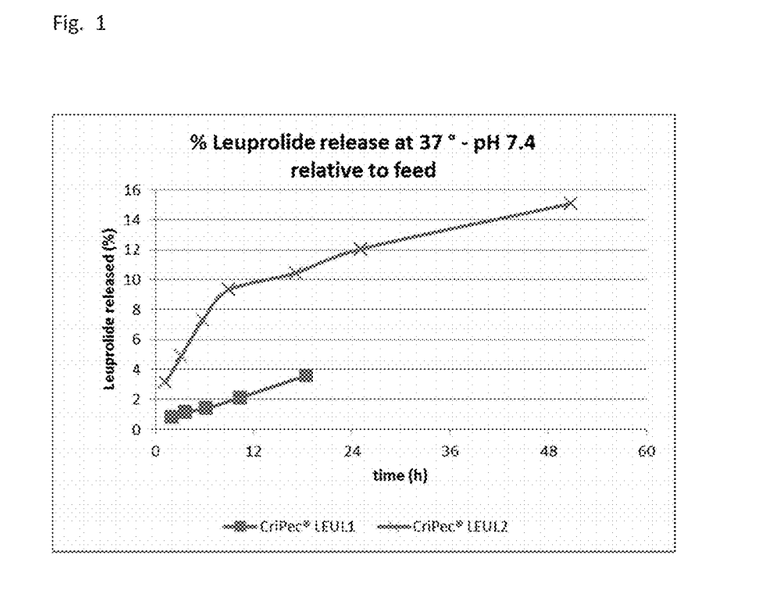
FIG. 1 Release of leuprolide over time, with different linkers as indicated.

Leuprolide is a peptide, and a rather hydrophilic compound. Controlled release is dependent on the type of linker used:

The particles are made as indicated in example 1 except that L1 is used as degradable linker. X is leuprolide and R=S whereas in L2 (example 1) R=SO. See also WO2012/039602. Body weight and behaviour of rats is evaluated to monitor safety FIG. 1 shows the release of Leuprolide over time, showing the tenability of the release by way of linker.

Figure 2:
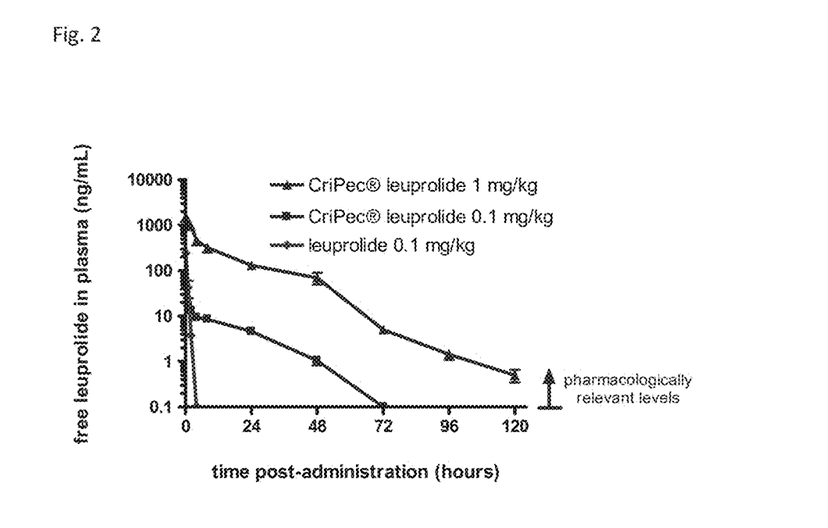
FIG. 2 PK profile, sustained release upon systemic exposure, dose response curve.

FIG. 2 shows the PK profile, sustained release upon systemic exposure, dose response curve.

Data is obtained after i v administration to healthy rats. Body weight and behaviour of rats is evaluated to monitor safety.

Example 3 Octreotide Covalently Entrapped in Micellar Nanoparticles

Cross-linked micelles with octreotide are made in the same way as the crosslinked micelles with leuprolide of example 1 or 2. Data is obtained after i.v. administration to healthy rats. Body weight and behaviour of rats is evaluated to monitor safety. Release of octreotide over time is measured as well as PK profile, sustained release upon systemic exposure, and dose response curve.

Example 4 Exenatide Covalently Entrapped in Micellar Nanoparticles

Cross-linked micelles with exenatide, a 39 amino acid peptide are made in the same way as the cross-linked micelles with leuprolide of example 1 or 2. Conjugation of the biodegradable linker occurs via amine-reactive linker to the lysine moiety of exenatide. Particles with a average size of 64 nm with a PDI of 0.03 were obtained. Release of the exenatide was measured in vitro under physiological condition. Exenatide was released over 4 days.

Example 5 Delivery of Antigen and Adjuvant Simultaneously to the DC Target Cell (e.g. Dendritic Cell)

Steps:
Adjuvant and antigen are derivatised by the same linker such as L1 or L2. The derivitised adjuvant and antigen are mixed with a thermosensitive polymer PEG-b-poly(N-hydroxyalkyl methacrylamide-oligolactates) with partially methacrylated oligolactate units, and cross-linked micelles are made essentially as described in example 1. The adjuvant and antigen are both entrapped co-valently inside the core of the nanoparticle.

The nanoparticle is purified by vivaspin or tangential flow filtration to remove any unconjugated adjuvant and/or antigen resulting in only 1 type of nanoparticle in solution.

The nanoparticle is tested in an animal model by i.v. administration in healthy rats, see also example 2. Release over time and PK profile is tested Controls are used: Body weight and behaviour of rats is evaluated to monitor safety. Antibody titres are measured.

Example 6 Tunable Particle Size

The particle of the present invention may be prepared in a very controlled way, either small (down to at least 30 nm) and even up to 80 nm. In all cases, these particles have a low polydispersity (i.e. lower than 0.2).

Block copolymers with HPMAmDPx (theoretical ratio between HPMAmDP1 and HPMAm2 is 53:47%) as thermosensitive block and mPEG$_{5000}$ as hydrophilic block were prepared by free radical polymerisation using (mPEG$_{5000}$) 2-ABCPA as macroinitiator essentially as described previously (Biomaterials 28 (2007) 5581-5593). In short, the concentration of the starting materials (monomers plus macroinitiator, varying ratios (mol/mol) were prepared) was 300 mg/mL in acetonitrile in airtight glass vials. The solution was flushed with nitrogen for at least 10 min, heated to 70° C., and stirred for 24 h. Next, by dropwise addition of the solution to an excess of diethyl ether, the polymers were precipitated. After centrifugation, the residue was dried in a vacuum oven. Afterwards, the polymers were dissolved in water and dialysed (membrane with a cut-off of 12-14 kDa) against water for at least 24 h with recovery by freeze drying.

Subsequently, methacrylate groups were coupled to parts of the thermosensitive block of mPEG-b-p((HPMAmDP1)-co-(HPMAmDP2)) by reaction of methacrylic anhydride with the terminal hydroxyl groups of the lactate side chains, also as previously described.

Figure 3:
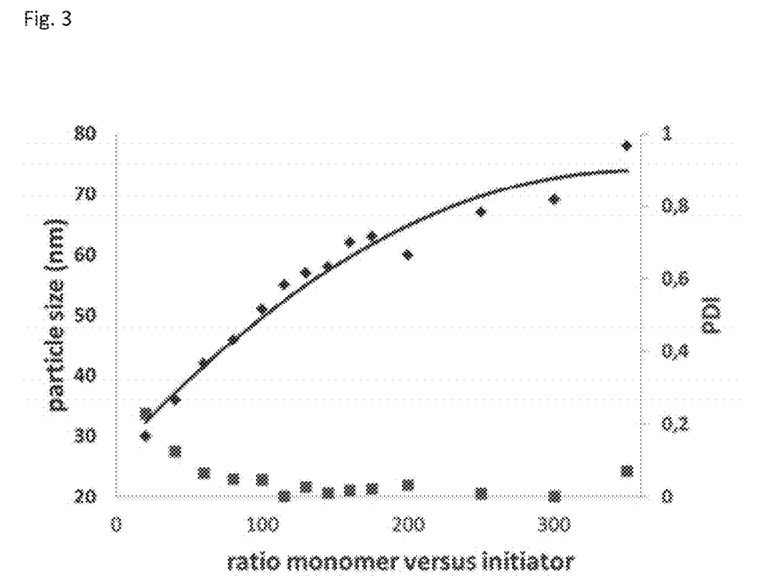
FIG. 3: particle size relative to monomer:initiator ratio and PDI of particles.

The obtained polymer lengths were very nicely controlled by using different monomer:initiator ratios, which in turn determined the particle size as plotted in the FIG. 3.

The invention claimed is:

1. A vaccine composition comprising a particle comprising a polymer matrix that covalently incorporates an adjuvant and/or antigen obtainable by a method which comprises the steps of
   (i) mixing an antigen and/or adjuvant comprising a first reactive moiety with an aqueous solution or dispersion comprising polymer chains, said polymer chains comprising at least one second reactive moiety capable of reacting with said first reactive moiety, wherein the first and/or second reactive moieties may be attached to the polymer chains or to the antigen and/or adjuvant through a linker and the polymer chains further being capable of cross-linking intra- or intermolecularly;
   wherein said polymer chains are subjected to conditions so as to self-assemble into particles either before or after said mixing, thereby entrapping said antigen and/or adjuvant non-covalently; thus obtaining the antigen and/or adjuvant encapsulated non-covalently in the particles;
   (ii) subjecting the particle mixture of step (i)
      (a) to cross-linking forming a particulate polymer matrix wherein the crosslinks of the matrix are independent of said antigen and/or adjuvant and
      (b) to conditions wherein said first and second reactive groups form covalent bonds so that the adjuvant and/or antigen is covalently entrapped in the particulate polymer matrix; and
      wherein the crosslinking is performed without free radical initiation and/or wherein the crosslinking is non-propagating.

2. The vaccine composition of claim 1 wherein steps (a) and (b) of step (ii) are performed simultaneously.

3. The vaccine composition of claim 1 wherein steps (a) and (b) of step (ii) are performed sequentially.

4. The vaccine composition of claim 1 wherein the cross-linking forms a bond selected from the group consisting of disulfide, ester, hydrazine, amide, Schiff-base, imine and acetal.

5. The vaccine composition of claim 1 wherein said method comprises a further step of conjugating the surface of the particle with a targeting agent and/or with an adjuvant and/or with an antigen.

6. The vaccine composition of claim 1 wherein the polymer chains in step (i) form polymer chain-rich phases in a continuous aqueous phase.

7. The vaccine composition of claim 6 wherein the adjuvant and/or antigen is present in a higher concentration in the polymer phases relative to the aqueous phase.

8. The vaccine composition of claim 7 wherein essentially all of the adjuvant and/or antigen is present in the polymer phases.

9. The vaccine composition of claim 1 wherein the polymer chains are thermo-sensitive polymer chains.

10. The vaccine composition of claim 9 wherein the adjuvant and/or antigen is mixed in the aqueous environment, and wherein the non-cross-linked polymer chains are initially present at a temperature lower than the Lower Critical Solution Temperature (LCST), after which the self-assembly is carried out at a temperature higher than the LCST; or at a temperature lower than the Critical Micelle Formation Temperature (CMT), after which the self-assembly is carried out at a temperature higher than the CMT.

11. The vaccine composition of claim 9 wherein the thermosensitive polymer chains are (co)polymers based on hydrophobically modified esters of N-hydroxyalkyl-(meth)acrylamide or N-(meth)acryloyl amino acids.

12. The vaccine composition of claim 9 wherein said thermosensitive polymers are (co)polymers of N-hydroxyalkyl methacrylamide-oligolactates or HEMAm (hydroxyethylmethacrylamide), alkyl-2-oxazolines, poly lactic acid (PLA)-methacrylate, methacrylated PLA-PEG-PLA or methacrylated PEG-poly caprolactone.

13. The vaccine composition of claim 9 wherein said polymers form micelles, hydrogels or microparticles.

14. The vaccine composition of claim 9 wherein the polymers are di- or triblock copolymers with PEG.

15. The vaccine composition of claim 1 wherein the reactive moieties are selected from the group consisting of alcohol, acid, amine, carboxyl, hydroxyl and hydrazine.

16. The vaccine composition of claim 1 wherein the polymer matrix is coupled to the antigen and/or adjuvant via a biodegradable bond or biodegradable linker.

17. The vaccine composition of claim 16 wherein the linker is of formula (1) or (2):

$$\text{HOQ-}(C_nH_{2n})\text{—S}(R^1)(R^2)\text{—}(C_mH_{2m})CH_2\text{-A,} \tag{1}$$

$$\text{or HR}^9\text{NQ-}(C_nH_2)\text{—S}(R^1)(R^2)\text{—}(C_mH_{2m})CH_2\text{-A} \tag{2}$$

wherein $R^9$ is H or $C_1$-$C_3$ alkyl wherein n and m are integers from 0 to 20;

wherein each of $R^1$ and $R^2$ is independently an electron lone pair, $=$O or $=$N—$R^X$, wherein each $R^X$ is independently selected from the group consisting of straight or branched $C_1$-$C_6$ alkyl, or straight or branched $C_2$-$C_6$ alkenyl or an aromatic moiety each optionally substituted by one or more substituents selected from the group consisting of halogen, hydroxyl, amino, amino substituted by one or two $C_1$-$C_3$ alkyl, carboxylic acid, nitro and cyano, wherein Q is a direct bond or C$=$O, C$=$NH or C$=$NR$^P$ wherein $R^P$ is $C_1$-$C_3$ alkyl; and wherein A is a polymerizable moiety methacrylate.

18. The vaccine composition of claim 1 wherein the particles have a polydispersity index (DPI) of less than 0.5.

19. A method to provide prophylactic or therapeutic treatment to a subject which comprises administering to a subject in need of such treatment an effective amount of the composition of claim 1 so as to induce an immune response.

* * * * *